US00PP11670P

United States Patent [19]

Heffner

[11] Patent Number: Plant 11,670

[45] Date of Patent: Dec. 5, 2000

[54] VARIETY OF PETUNIA NAMED 'TRUMPET CHIFFON'

[75] Inventor: Mike Heffner, Lompoc, Calif.

[73] Assignee: John Bodger and Sons Company, South El Monte, Calif.

[21] Appl. No.: 09/169,795

[22] Filed: Oct. 9, 1998

[51] Int. Cl.[7] ..... A01H 5/00

[52] U.S. Cl. ..... Plt./356

[58] Field of Search ..... Plt./356

[56] References Cited

U.S. PATENT DOCUMENTS

P.P. 10,310 3/1998 Sakazaki ..... Plt./356

*Primary Examiner*—Bruce R. Campbell
*Assistant Examiner*—Wendy A Baker
*Attorney, Agent, or Firm*—Fulwider Patton Lee & Utecht, LLP

[57] ABSTRACT

The claimed cultivar brings a new color to the Trumpet series of Petunias and is characterized by a deep salmon colored flower delicately accented at its center with green over a medium green foliage. As with all Trumpet Petunias, this cultivar exhibits early flowering with superior branching so that the plant may also be used in a hanging pot.

1 Drawing Sheet

BACKGROUND OF THE NEW PLANT

The present invention relates to a new and distinct variety of Petunia known by the name 'Trumpet Chiffon' (Bodger No. 7P3356-2). The new variety was discovered in a selective breeding program by Mike Heffner at Bodger Seeds, Ltd., Lompoc, Calif. The new variety is a selection from the crossing of inventor's proprietary Petunia selection Bodger No. 7P626-2 (unpatented) which is a seedling with spreading decumbent habit and small salmon colored flowers, with inventor's proprietary Petunia selection Bodger No. 7P1100-3 (unpatented) which is a seedling with upright habit and large pink flowers.

This new variety is the result of a breeding program whose objective was to develop new vegetatively propagated petunias with a spreading cascading habit, large flowers and with a color range not presently available as a cutting product. The variety originated from a cross between two proprietary seedling selections taken from the existing breeding program. The progeny from this cross was grown out during the summer of 1997 and a number of single plants were selected as possible new varieties and propagated vegetatively. The cuttings were trialed and evaluated during winter and summer of 1998 at which time it was determined that this particular line, established from one single plant, was distinguishable and unique.

The new cultivar was first asexually reproduced by terminal vegetative cuttings at Bodger Seeds, Ltd., Lompoc, Calif. and has been repeatedly asexually reproduced by cuttings at Bodger Seeds, Ltd.,at Lompoc Calif. It has been found to be stable and true to type through successive propagations.

The new cultivar was grown in a glass greenhouse in Lompoc, Calif., using full light, 60° Fahrenheit night temperature, 77° Fahrenheit day temperature, and grown in soil having a temperature of 80° Fahrenheit. The claimed plant was grown from a terminal vegetative cutting, and exhibited an eight to ten weeks response time from an unrooted cutting to a 25 cm flowering plant.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Bodger Seeds Ltd. In Lompoc, Calif. The plant histories were taken on rooted cuttings believed to have been potted in a 25 cm pot, under full light in the greenhouse, and color readings were taken in in day light using The Royal Horticultural Society of London Colour Chart.

THE PLANT

Classification:
- *Botanical.*—*Petunia×hybrida Hort.*
- *Commercial.*—'Trumpet Chiffon' petunia.

Form: Indeterminate with spreading and decumbent habit. When planted in a hanging pot the stems hang down.
- *Height.*—19 cm above the top of pot.
- *Spreading area of plant.*—112 cm in diameter.

Foliage: Freely branching.

Leaves: Leaves are simple, opposite at base and tip of stem, alternate in center; pinnate venation; foliage viscid; leaves horizontal to stem; numerous shoots at internodes.
- *Size.*—7.4 cm length when fully expanded. 4.9 cm width when fully expanded. 0.5 mm thickness.
- *Shape.*—Ovate.
- *Margin.*—Entire.
- *Texture.*—Sparsely pubescent.
- *Color.*—Upper: Green Group 137B. Lower: Yellow-Green Group 146A.
- *Apex.*—Obtuse.
- *Base.*—Attenuate.

Stem:
- *General.*—Hanging; Spreading to a length of 56 cm.
- *Color.*—Yellow-Green Group 144B.
- *Internode length.*—3.3 cm.
- *Diameter.*—0.4 cm.
- *Anthocyanin pigmentation.*—Absent.
- *Texture.*—Pubescent.

INFLORESCENCE

Young flower:
- *Diameter.*—5.3 cm.
- *Length.*—4.9 cm.

*Color.*—Inside: Red-Purple Group 61D with a greenish circular area in center of Yellow-Green Group 150D; center circular area diameter 1.4 cm. Outside: Red Group 56B at the upper portion; Yellow-Green Group 150B on the lower portion.

Mature flower:

*Diameter.*—9.0 cm.

*Length.*—5.9 cm.

*Color.*—Inside: Red Group 55B with a distinctive Yellow-Green Group 150D area in the center; center circular area diameter 2.1 cm. Outside: Red Group 56B at the upper portion; Yellow-Green Group 150B on the lower portion.

Open florets:

*Form.*—Single funnelform flowers; calyx five parted, petals united into flower tube; petal apex broadly acuminate to rounded.

*Texture and appearance.*—smooth on inside, pubescent on outside, presenting large salmon flowers.

Pedicel:

*Length.*—3.6 cm.

*Thickness.*—0.3 cm.

*Texture.*—Pubescent.

Sepals:

*Quantity.*—5.

*Length.*—2.7 cm.

*Width.*—1.6 cm.

*Shape.*—Elliptic.

*Color.*—Inside: Green Group 137A. Outside: Green Group 137C.

*Apex.*—Obtuse.

*Margin.*—Entire.

*Texture.*—Pubescent.

Persistence:

*Disease resistance.*—No known special disease resistance compared with other Petunias.

REPRODUCTIVE ORGANS

Stamens:

*Number.*—5 normal stamens.

*Anthers.*—4 level with stigma; 1 below stigma.

*Filaments.*—White.

Pistils:

*Number.*—1 normal.

*Stigma.*—Green.

*Style.*—Yellow-green.

Ovaries: Superior.

GENERAL CHARACTERISTICS

'Trumpet Chiffon' brings a new and distinct color to the Trumpet Series of Petunias which is a group of varieties that are early flowering and very floriferous having large blooms with numerous branching at internodes. At maturity 'Trumpet Chiffon' has approximately 150–200 open blooms per 25 cm pot. 'Trumpet Chiffon' presents a large Salmon colored flower delicately accented with shades of green at its center. The flowers open above the foliage and face outwards and have no fragrance. The variety shows normal fertility and seed set.

I claim:

1. A new and distinct variety of Petunia plant, substantially as shown and described.

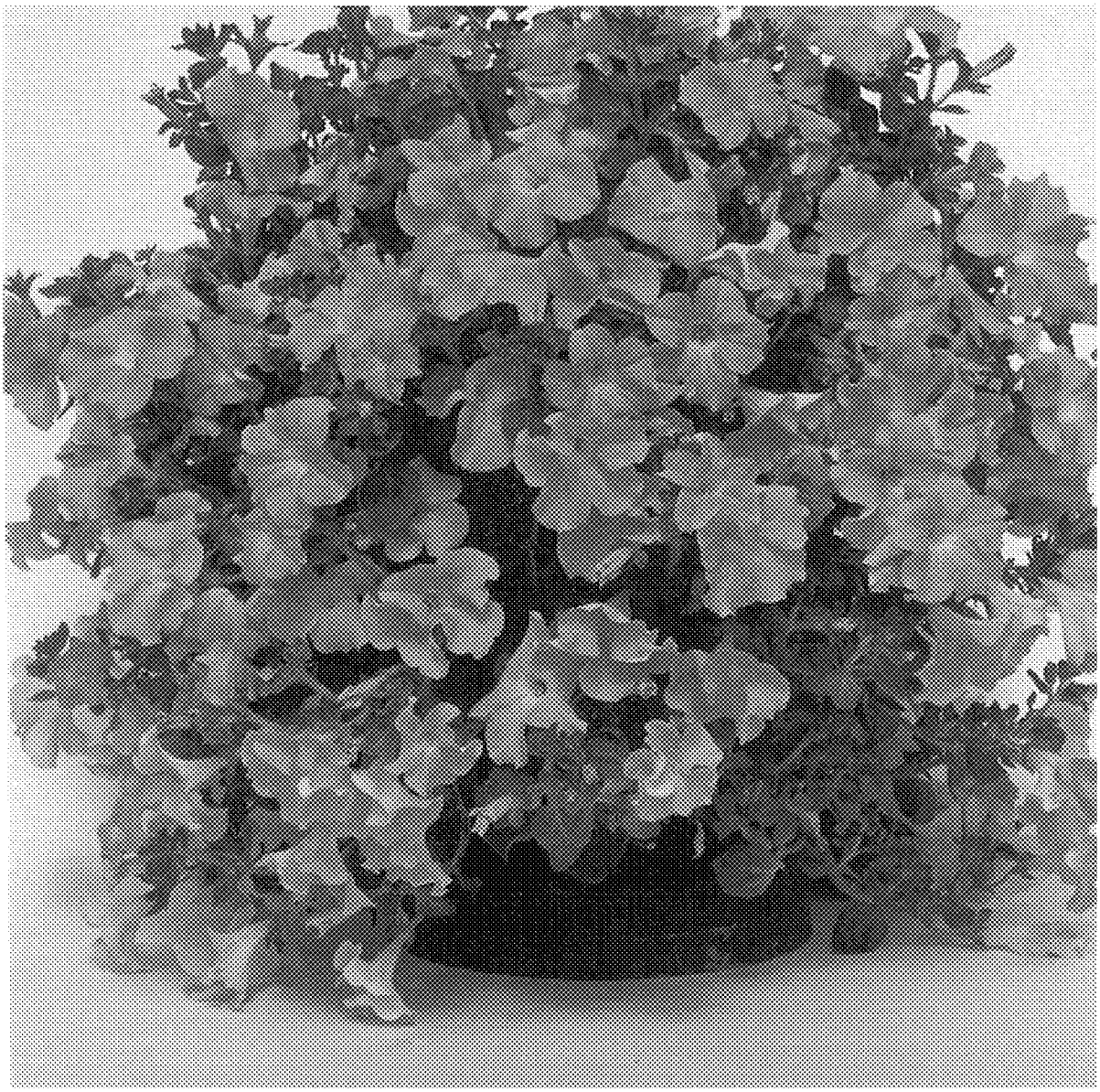

* * * * *